United States Patent [19]

Bredeweg et al.

[11] 4,290,296
[45] Sep. 22, 1981

[54] METHOD AND APPARATUS FOR GAS DOSING FOR LINEARIZATION

[75] Inventors: Roger L. Bredeweg; George J. Sitek, both of Stevensville, Mich.

[73] Assignee: Leco Corporation, St. Joseph, Mich.

[21] Appl. No.: 95,508

[22] Filed: Nov. 16, 1979

[51] Int. Cl.$^3$ .............................................. G01N 31/00
[52] U.S. Cl. .................................................... 73/1 G
[58] Field of Search ...................... 73/1 G, 23; 137/93, 137/883; 250/343

[56] References Cited

U.S. PATENT DOCUMENTS

| | | | |
|---|---|---|---|
| 3,776,023 | 12/1973 | Budd et al. | 73/1 G |
| 3,882,713 | 5/1975 | Nishida et al. | 73/23 |
| 3,948,281 | 4/1976 | Strain et al. | 137/93 |
| 4,177,835 | 12/1979 | Paley | 137/883 |
| 4,191,215 | 3/1980 | Gonner | 137/883 |

OTHER PUBLICATIONS

K. J. Parkinson et al., "A New Method for Calibrating Infrared Gas Analysers", *Journal of Physics E,* pp. 598–600, vol. 4, Aug. 1971.

*Primary Examiner*—Stephen A. Kreitman
*Attorney, Agent, or Firm*—Price, Heneveld, Huizenga & Cooper

[57] ABSTRACT

A combustion analyzer for the analysis of the carbon and sulfur content in steel includes a gas flow system whereby a carrier gas flows through a combustion chamber and gaseous by-products of combustion flow through one or more infrared cells for analysis. In order to correct for the inherent nonlinearity of the measurement of concentration by the infrared cell or cells, a linearity correction system is provided. In the linearity correction system, discrete levels of concentration of known gases are dosed into the system and the detected concentration measured. Scaling factors are determined by an iterative process employing a microprocessor which scaling factors are then employed to correct for the nonlinearity in sample measurements. In one embodiment of the invention, the flow of the specimen gas employed for dosing the system is measured as a function of the pressure differential across a given size flow restrictor using an improved control valve and dosing manifold.

22 Claims, 8 Drawing Figures

METHOD AND APPARATUS FOR GAS DOSING FOR LINEARIZATION

BACKGROUND OF THE INVENTION

The present invention relates to a dosing system for combustion analyzers and particularly to a method and apparatus for correcting for nonlinearities in the display of the concentration of specimen gases.

In analyzers for the analysis of, for example, carbon and sulfur content in steel, absorption infrared cells are employed. As the concentration of the gases representing the carbon and sulfur content ($CO_2$ and $SO_2$ respectively) increase; the output signals from the infrared detectors vary in a non-linear fashion. Due to the fact that narrow band pass filters are employed, the output signals from the detectors do not follow the predictable logarithmic Beer's law curve for concentration. Accordingly, in order to provide reproducible and accurate readouts of detected concentrations of $CO_2$ and $SO_2$ representative of the carbon and sulfur content respectively of an unknown specimen; it is necessary to linearize the electrical signals from the detectors.

In the past with flow through type analyzers such as model CS-44, commercially available from Leco Corporation of St. Joseph, Mich., an electrical analog multiplier circuit was employed to provide a second order approximation in an effort to correct linearity. The circuit operates to provide a linear output signal to a point and then begins multiplying the input signal by a continually increasing value. This provided a linearity of approximately five percent which although an improvement over uncorrected systems, did not provide accuracy capable of achievement by the system of the present invention.

SUMMARY OF THE INVENTION

The system of the present invention corrects for linearity by providing a gas dosing system whereupon dosing gases comprising a known mixture of gases to be analyzed is introduced into the gas flow path of the system at a plurality of known concentration levels. The detector output signals are applied to a microprocessor having an algorithm which determines scaling factors for the plurality of concentrations. The scaling factors are then employed to correct for nonlinearity of any unknown gas concentrations falling along the corrected response curve determined by the dosing gases. In one embodiment of the present invention, the concentration level of the dosing gases is accurately ascertained by measuring the differential pressure across previously calibrated restrictors in the gas doser to determine concentration. In order to maintain the dosing gas volume within the dosing system control to a minimum for quick and accurate control of dosing, a unique integral valve and manifold is employed according to one aspect of the invention.

By employing the system of the present invention, greatly improved linearization approximating plus or minus 0.5 percent is achieved. These and other features, objects and advantages of the present invention will become apparent upon reading the following description thereof with reference to the drawings in which:

DETAILED DESCRIPTION OF THE PREFERRED EMBODIMENT

Figure 1:
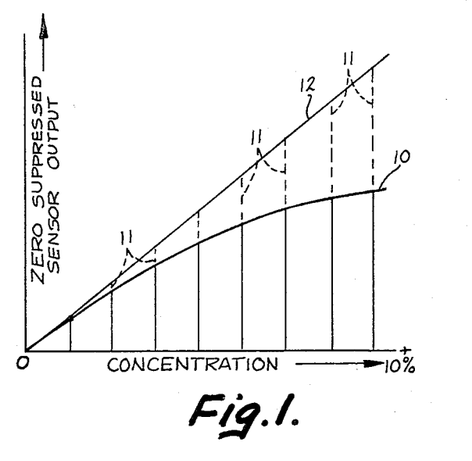
FIG. 1 is a diagram illustrating the desired and zero suppressed output signals from an infrared detector.

Referring initially to FIG. 1 there is graphically represented a typical zero suppressed infrared detector output signal 10 with respect to either $CO_2$ or $SO_2$ detectors plotted against concentration. Typically, the concentration will vary from 0 to, for example, 10 percent concentration by weight shown at the right end of the concentration scale. As can be seen, the curve 10 falls off in a nonlinear fashion with increasing concentration. This nonlinearity is inherent in infrared cells employing detectors and filters for the measurement of absorption spectra from specimen gases. It is to be understood that the graphic representation of FIG. 1 is not intended to represent the exact response curve of a particular detector but is illustrative only.

It is desired to provide reproducible and accurate analysis results to compensate for the nonlinearity response curve of the infrared detectors to correct the nonlinear curve 10 to at least a piecewise linear curve such as represented by the straight line 12 of FIG. 1. This is achieved in the present invention by providing a series of scaling factors used to modify the detected signal output from the sensor such that it will fall on line 12 for all detected levels of concentration. For increasing concentration levels there will be an increasing difference in the desired output signal 12 from the actual output signal 10 as represented by the dotted line 11. The response curve 10 is divided into eight segments by breakpoints (Bk in FIG. 1) at certain concentration levels. The correct signal desired for a linear response falls on line 12 and is referred to as an adjusted breakpoint (Adj. Bk). In order to determine the scaling factors, a gas dosing system is employed in which a known concentration of known purity gas(es) is injected or dosed into the infrared cells at different levels, the IR cell output measured, and the scaling factor for each level is calculated to provide a linear output signal for the varying concentrations.

Figure 2:
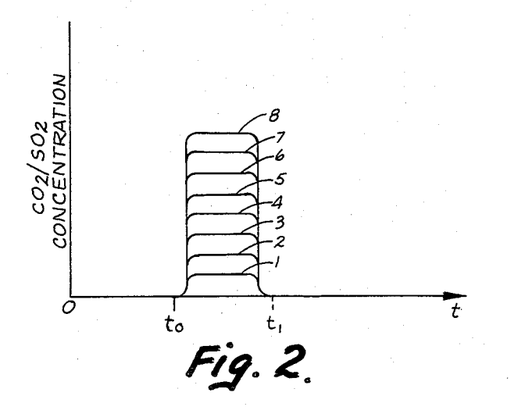
FIG. 2 is a concentration diagram showing the manner by which specimen gas dosing is achieved in the system of the present invention.

FIG. 2 represents the manner by which the gas dosing is achieved whereupon predetermined flow rates of gas are metered into the stream of gas flowing in the system between a fixed time period t0 to t1 successively at eight different times to provide eight increasing levels of concentrations 1–8. In a preferred embodiment it has been found that the time t0 to t1 is selected to be approximately 20 seconds during which a mixture of specimen gas constituting 95% carbon dioxide to 5% sulfur dioxide is metered into the analyzer. As additional 20 second pulses of increasing flow rates of gas are supplied to the system, the stepwise increasing concentration as illustrated in FIG. 2 is achieved for the eight different levels of concentration of interest. For each of the concentration levels, a scaling factor (SI) is determined such that a linear response line 12 (FIG. 1) can be calculated by the microprocessor of the preferred embodiment. When measuring a sample of unknown concentration, the system detects the actual sensor output and applies the scaling factor appropriate for the concentration level detected to provide a signal for display which responds linearly with varying concentrations. In the preferred embodiment, the manner by which the gas dosing is achieved is unique and employs the flow system illustrated in FIG. 3 together with a gas dosing manifold and associated valves illustrated in FIGS. 4 and 5 which are now described.

Figure 3:
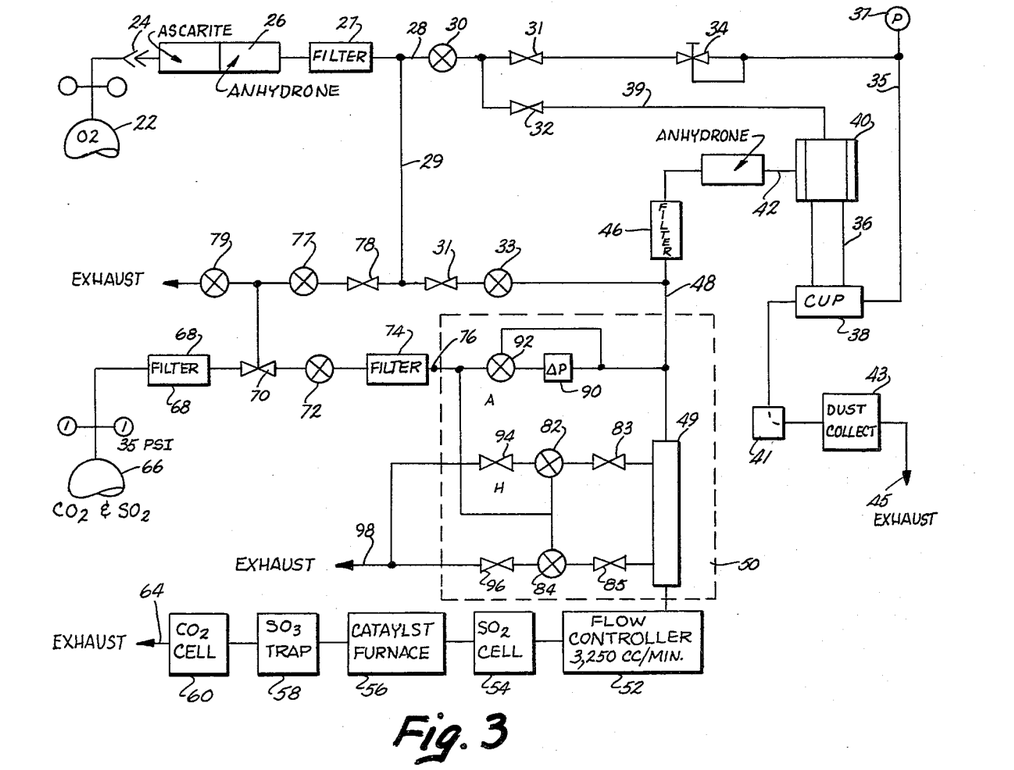
FIG. 3 is a diagram partly in schematic and block form of the gas flow path in an analyzer embodying the present invention.

Referring to FIG. 3, there is shown an analyzer incorporating the gas dosing system of the present invention. The flow system for the oxygen carrier gas includes a source 22 supplying oxygen through a suitable connector 24 to an ascarite filter 25 which removes any residual $CO_2$ from the oxygen source. Coupled in series with the ascarite filter is an anhydrone filter 26 for removing water from the oxygen carrier gas stream. Coupled to the outlet of the anhydrone filter 26 and in series therewith is a dust filter 27. The output of the dust filter thus is a stream of oxygen with water, $CO_2$ and dust removed therefrom to supply oxygen to the combustion system of the analyzer through a conduit 28 and to the gas dosing portion of the analyzer through a conduit 29.

Oxygen is supplied to the combustion chamber through conduit 28 by means of valve 30 which is solenoid controlled and a pair of flow restrictors 31 and 32. Restrictor 31 is coupled to a combustion pressure adjustment valve 34 and subsequently to the lower end of the combustion chamber constituting a combustion tube 36 and a sealing cup 38. The lower end of the combustion system includes an exhaust conduit 39 leading to a pinch valve 41 which can be selectively opened to instantaneously lower the pressure in the chamber causing a flow of oxygen downwardly through conduit 39 thereby forcing dust accumulated therein to be collected by dust collecting chamber 43. The oxygen is filtered by the dust collecting chamber 43 and then exhausted through exhaust port 45. Tube 36 is generally a cylindrical quartz tube surrounded in the preferred embodiment by a RF frequency actuated induction coil (not shown) for heating a solid specimen such as steel contained within a ceramic crucible to temperatures of about 1700° F. to burn the specimen in an oxygen atmosphere to provide a gaseous specimen for analysis. The details of the construction of the combustion chamber, its ceramic crucible, combustion tube, induction coil and associated mechanism are disclosed in greater detail in co-pending U.S. patent application, Ser. No. 016,975 filed Mar. 2, 1979, now U.S. Pat. No. 4,234,541, and entitled COMBUSTION CHAMBER CLEANING APPARATUS, the disclosure of which is incorporated herein by reference.

A pressure gauge 37 coupled in the conduit 35 between pressure regulator 34 and combustion chamber 36 is provided for monitoring the combustion chamber pressure which in the preferred embodiment is selected by pressure regulator 34 to fall within the range of 10–12 psi to provide oxygen for the combustion of a specimen. In addition to the gas supplied to conduit 35, gas from source 22 is also supplied to the combustion chamber 36 through flow restrictor 32, conduit 39 coupled to a manifold 40 on the upper end of combustion chamber 36 and an oxygen lance (not shown) which directs a stream of oxygen into the open mouth of the ceramic crucible to insure complete combustion of the specimen.

The by-products of combustion exit the manifold 40 by conduit 42 and enter anhydrone filter 44 for removal of water therefrom and through a dust filter 46 where they enter input 48 of gas dosing manifold 49. Manifold 49 is an integral part of the gas dosing manifold and valve assembly 50 indicated in FIG. 3 by the structure surrounded by dotted lines. The by-products of combustion then pass through conduit 100 (FIGS. 4 and 5) in manifold 49 through outlet 51 thereof and into a flow controller 52 serially coupled in the flow path and set to control the flow rate at 3,250 cc per minute. The flow controller is coupled to a $SO_2$ infrared detector cell 54 including an infrared detector 55 (FIG. 8) and thence to a serially connected catalyst furnace 56 which is a resistance heating furnace heated to approximately 350° C. for converting any remaining CO to $CO_2$. An $SO_3$ trap 58 collects the $SO_3$ that results from this process. The remaining by-products of combustion are then supplied to the serially coupled $CO_2$ infrared detecting cell 60 including an infrared detector 62 (FIG. 8) and exhausted to the atmosphere through an exhaust port 64. Supply 22 is also used for the purging of contaminates from the system by conduit 29. The purging gas flows through a flow restrictor 31 and a purging valve 33 which when opened, provides a 10 liter per minute flow rate for approximately 5 seconds back flushing filter 46 and filter 44 and flowing through chamber 36 and out through conduit 39. Some of the purging gas also flows through the gas dosing system through conduit 48 to purge the dosing manifold 49 as well as the infrared cells 54 and 60 and the associated conduits.

The dosing gas supplied for the gas doser 50 constitutes a mixture of 95% $CO_2$ and 5% $SO_2$ provided by source 66 coupled to the gas dosing unit 50 by means of a first filter 68, a pressure regulator 70, and a 3-way valve 72 employed to apply the dosing gas. When valve 72 is in the gas dosing position, the dosing gas is applied through filter 74 to input 76 of the dosing unit 50.

To control the flow of dosing gas from source 66 to input 76 of the dosing unit 50, the dosing gas pressure is varied by pressure regulator 70 which is pneumatically controlled by pressure applied by conduit 71 from the oxygen supply conduit 29. Conduit 29 is coupled to a pressure increasing valve 77 through a flow restrictor 78 to increase the pressure of dosing gas and therefor flow as valve 77 is opened and regulator 70 provides a greater pressure of dosing gas. The amount of gas dosing flow is reduced by opening valve 79 which exhausts oxygen from the controlling conduit 71 thereby reducing the pressure supplied to the controlling element of pressure regulator 70 to reduce the pressure and thus the flow of dosing gas supplied to input 76 of the dosing system 50.

The flow of dosing gas within unit 50 follows the path shown by arrows A through conduit 80 into a branch conduit 81 to a pair of valves 82 and 84 associated with a first relatively large flow restrictor 83 and a second relatively small flow restrictor 85 respectively. Valves 82 and 84 and flow restrictors 83 and 85 are mounted directly to the gas dosing manifold 49 as shown schematically in FIG. 3 and as shown in greater detail in FIGS. 4 and 5 as subsequently described. Valves 82 and 84 are solenoid valves selectively actuated by control signals from the microprocessor shown in FIG. 8 to provide eight levels of gas dosing as shown in FIG. 2.

To monitor the flow of gas provided, a solid state pressure transducer 90 is mounted directly to manifold 49 and provides a range of 0 to +15 psi measurement. Transducer 90 is selectively inserted across the restrictors 83 and 85 by means of conduits 48' and 93 and by a valve 92 which when in a first position couples the transducer 90 to conduit 48' for monitoring the combustion chamber pressure and when in a second position couples the transducer between conduit 48' and input conduit 93 coupled to the dosing gas supplied to restrictors 83 and 85. Valves 82 and 84 are both 3-way valves which selectively exhaust the dosing gases through flow restrictors 94 and 96 and through an exhaust port 98 when valves 82 and 84 decouple conduit 80 from restrictors 83 and 85 and couple conduit 80 to restrictors 94 and 96. Pressure transducer 90 is a silicon transducer commercially available from National Semiconductor Corporation to provide an electrical output signal as a function of pressure detected. When valve 92 is in an energized state, the pressure transducer input and output are fed back on themselves such that the transducer reads 0 and provides a 0 point for calibration. When valve 92 is deenergized (i.e. in an open position), the left side of transducer 90 as seen in FIG. 3 is coupled to input 76 of the gas dosing system to either measure the pressure differential across restrictors 83 and 85 or when valve 72 is vented to the atmosphere, measure the combustion pressure of conduit 48.

To achieve the eight levels of gas dosing illustrated by FIG. 2, valves 77, 79, 82 and 84 are selectively actuated as follows. Initially, valve 84 is actuated such that gas dosing is achieved for a period of about 20 seconds through the small restrictor 85 into the manifold 49. Valves 77 and 79 are selectively actuated to control regulator 70 to provide four different levels of gas dosing pressure to provide a pressure differential measured by transducer 90 across orifice 85 of 1.65 psi, 4.2 psi, 8.4 psi, and 13.5 psi. For the last four levels (5–8) of concentration of gas dosing, valves 82 and 84 are both open such that an additional amount of dosing gas flows through the larger restrictor 83 as well as the smaller restrictor 85 with the pressure transducer 90 reading a pressure of 5.1 psi, 7.5 psi, 10.2 psi, and 14.1 psi for the remaining four levels of concentration in the preferred embodiment. In order to precisely control the volume of gas entering the manifold 49, it is desirable that the conduits, valves and flow restrictors, including valves 82, 84 and 92 and restrictors 83, 85, 94 and 96 be placed in close proximity with manifold 49 and occupy the smallest volume possible such that actuation of the valves will provide a substantially simultaneously change in the flow of dosing gas to the system. In order to achieve this result, an integral manifold and valve system is employed as shown in detail in FIGS. 4 and 5 now described.

Figure 4:
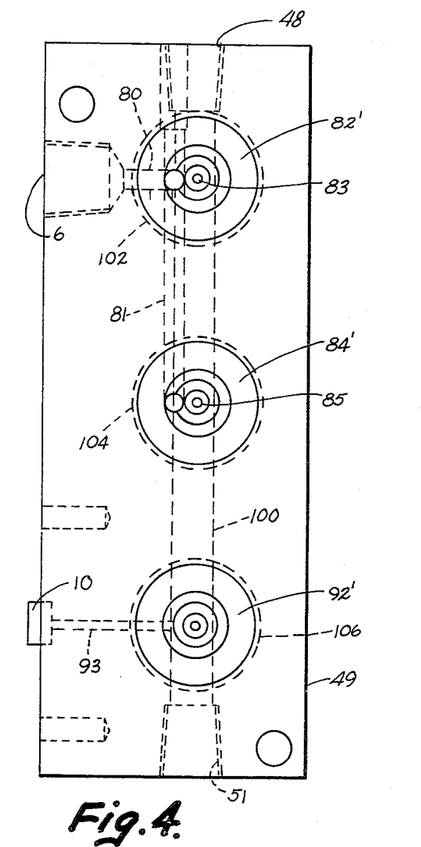
FIG. 4 is a top plan view of a manifold in the system of the present invention.
Figure 5:
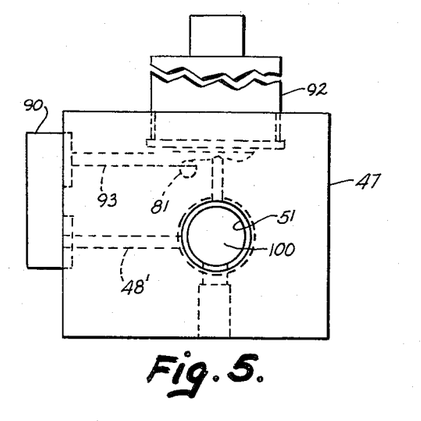
FIG. 5 is a front elevational view of the manifold shown in FIG. 4 including a valve mounted thereto.

Referring now to FIGS. 4 and 5, the elements of the gas dosing assembly 50 shown in FIGS. 4 and 5 corresponding to those elements shown in FIG. 3 are correspondingly numbered. Manifold 49 comprises a generally rectilinear elongated body having an aperture 100 machined longitudinally therethrough with inlet port 76 formed inwardly therein at one end and communicating with conduit 80 and transverse conduit 81 coupled between valves 82 and 84, the valve seats for which are shown in FIG. 4 as 82' and 84' respectively. Valves 82, 84 and 92 are identical plunger valves commercially available from Gould Allied Control, model 331X-5 which are solenoid actuated valves for opening and closing the valves as previously described. The valves are threadably secured within threaded apertures 102, 104 and 106 formed in the manifold for securing the valves directly to the manifold such as valve 92 shown in FIG. 5. Inlet 48 is formed in the manifold 49 at one end of aperture 100 while outlet 51 is formed at the opposite end.

Pressure transducer 90 is mounted to the side of the manifold as best seen in FIG. 5 and has pressure sensitive elements which with conduits 93 and 48' formed in manifold 49 and communicating with valve 92 and aperture 100 to provide a differential pressure reading between these two locations as described above. The flow restrictors 83 and 85 are commercially available sintered metal restrictors press fit into the centers of valve seats 82' and 84' respectively. The restrictors 83 and 85 are one quarter-inch in diameter and provide a flow rate of 240 cc per minute and 100 cc per minute respectively with a pressure differential there across of between 10–12 psi. Restrictors 94 and 96 are also sintered metal restrictors which are fitted directly on valves 82 and 84 through standard couplings which provide an open end defining exhaust port 98.

Thus, manifold 49 provides an integral support means for the valves for providing an extremely accurate stepwise increasing flow of dosing gas into the gas detection elements of the analyzer. The utilization of an integral manifold with flow restrictors and pressure measuring means assures that actuation of the respective valves associated with the manifold provides a nearly instantaneous change in the amount of dosing gas so that accurate and reproducible results can be achieved. The design thus provides a gas doser with a minimum of volume occupied by the in an extremely accurate structure for dosing the specimen gas with known concentrations of a dosing gas.

Figure 6:
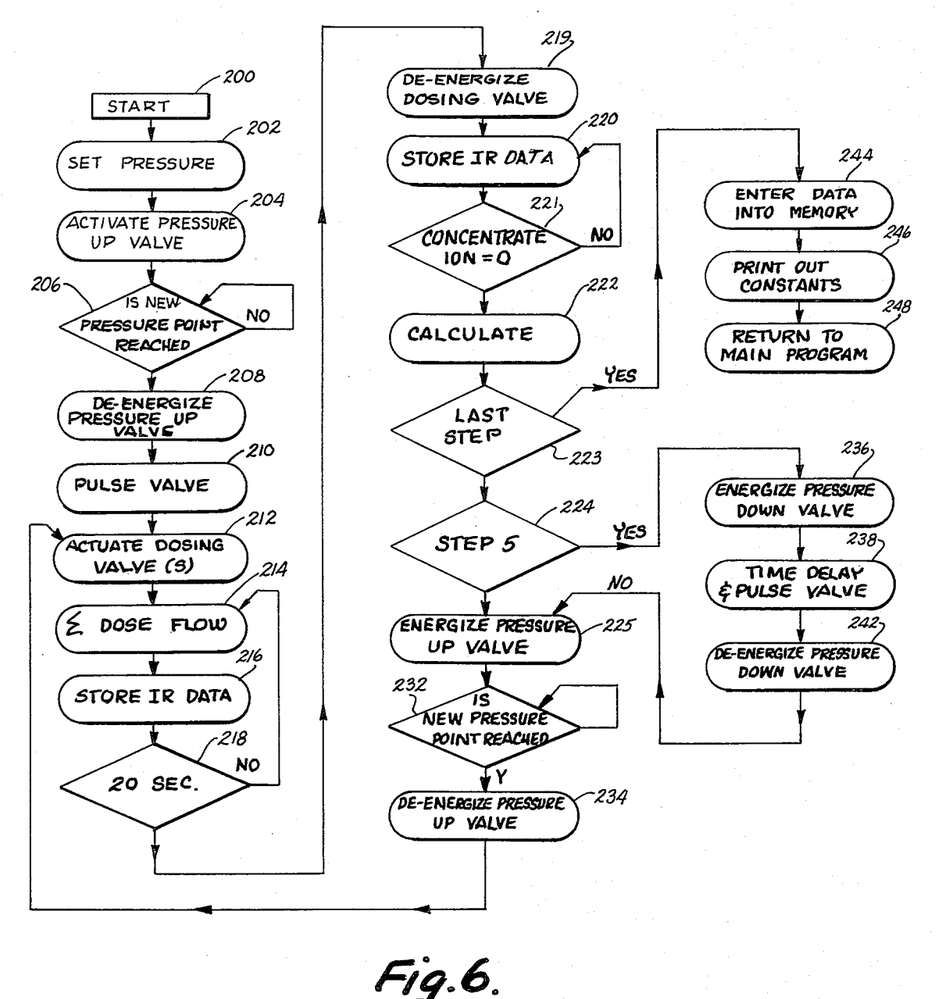
FIG. 6 is a flow diagram of an algorithm for the microprocessor of the present invention.
Figure 7:
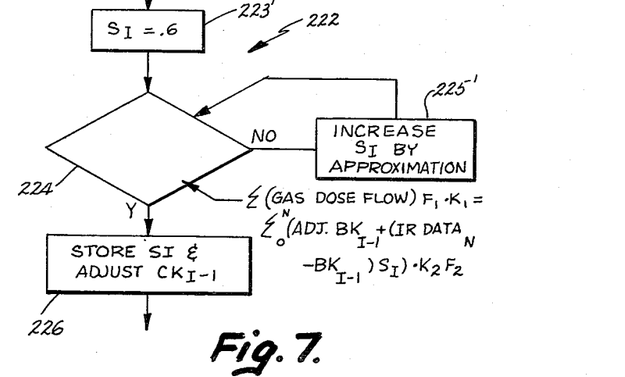
FIG. 7 is a detailed flow diagram of a portion of the diagram shown in FIG. 6.
Figure 8:
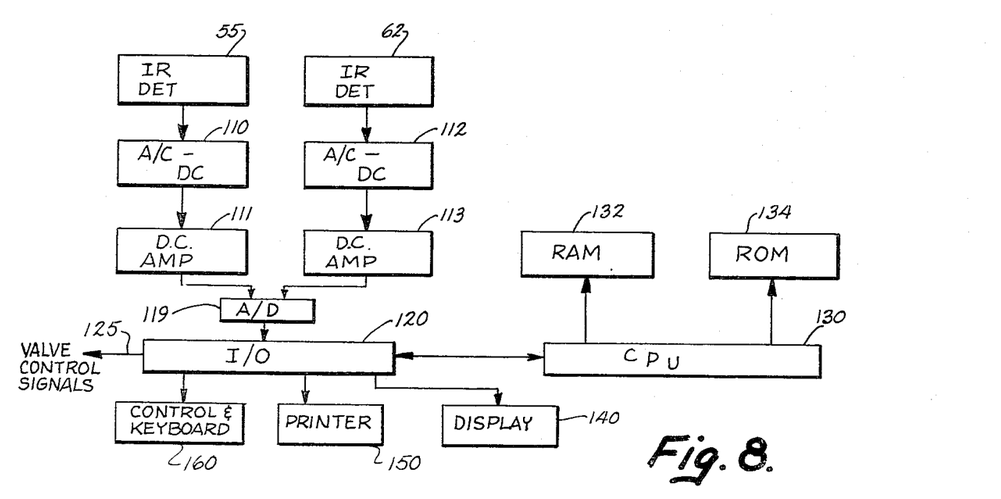
FIG. 8 is an electrical circuit diagram in block form of an analyzer embodying the present invention.

Before describing the operation of the system in conjunction with FIGS. 3, 6 and 7, a brief description of the electrical circuit components used to control the analyzer is presented in connection with FIG. 8. The infrared detectors 55 and 62 for $SO_2$ and $CO_2$ respectively provide alternating current signals which are applied to AC to DC converters 110 and 112 respectively and then to DC amplifiers 111 and 113 to provide a DC input signal to an A/D converter to provide a digital signal to an input/output circuit 120. Input/output circuit 120 as is well known, includes a series of standard data processing and handling circuits to provide the necessary data format to interface between the various inputs and outputs and the central processing unit (CPU) 130. Associated with the CPU 130 is a RAM memory 132 and a ROM memory 134 employed for temporarily storing data and for providing a permanent program for controlling the analyzer respectively. The input/output circuits 120, CPU 130, and memories 132 and 134 respectively make up the microprocessor which in the preferred embodiment employs an Intel type 8085 integrated circuit. Also coupled to the input/output circuits 120 is a display 140 employed to display the concentration results as well as other information pertaining to system operation. A printer 150 provides a hard copy of information desired and also displayed by the display 140. A control and keyboard panel 160 is provided and includes a conventional keyboard as well as other keying functions for operation of the system. The input/output circuit 120 includes an output bus 125 which provides timing and control signals for actuating the gas dosing control valves in the manner now described in conjunction with the flow diagrams of FIGS. 6 and 7 showing in a structure of the ROM program for controlling the microprocessor to achieve the gas dosing linearization information later used for analysis of unknown specimens.

In conjunction with the flow diagrams of FIGS. 6 and 7, it is to be understood that this represents one of many possible programming sequences which can be used to control the gas dosing system of the present invention. The linearization program shown in FIG. 6 is initiated by the operator actuating a linearization command switch on keyboard 160 to start the program as indicated by block 200 in FIG. 6. Subsequently, as indicated by block 202, valve 72 is actuated such that the pressure transducer 90 will measure the combustion chamber pressure. Subsequently valve 92 is actuated such that the 0 pressure level reading can be stored in memory. Next the pressure increase valve 77 is actuated as indicated by block 204 to increase the gas dosing pressure by actuating regulator 70 to one of the selected eight levels. The first pressure level is sensed by transducer 90 and compared with a predetermined level by the program as indicated by comparison block 206 and valve 77 remains actuated until the desired level is reached at which time, as indicated by block 208, valve 77 is deenergized. Next, valve 72 is pulsed as indicated by block 210 for several cycles of one second pulses such that the supply of dosing gas can purge the system of any gases remaining from previous operation of the unit. At this time, valves 82 and 84 are closed and the gas flow path for the pulsing purging gas from source 66 flows through inlet 76 through valves 82 and 84 out through flow restrictors 94 and 96 through the exhaust port 98. When actuated, valves 82 and 84 close off restrictors 94 and 96 and couple the dosing gas supply through restrictors 83 and 85 depending upon the position of these valves.

Next, as indicated by block 212, the microprocessor generates a command signal to selectively actuate, depending upon the pressure level reached, valve 82 and/or valve 84 to initiate the flow of dosing gas into manifold 49 where it mixes with the carrier gas stream from source 22. During this period of time which as indicated by blocks 214 and 216, the pressure transducer 90, as noted earlier, provides the pressure output signals in direct relationship to the flow of gases through the flow restrictors 83 and 85. Thus, as indicated by block 214, during the twenty-second period for each level of gas dosing, samples of the pressure and therefore the flow rate are taken at a 60 millisecond sample rate and summed to provide a total volume of gas injected during the gas dosing process. As indicated by block 216, data from the infrared detectors 55 and 62 are simultaneously taken and stored in the RAM memory 132. The dosing continues until the twenty-second period has elapsed as indicated by block 218 and the dosing valve is deenergized (219). IR data collection (block 220) continues until the sample gas concentration goes to zero (block 221). The calculations (block 222) are then made after which a check is made as indicated by blocks 223 and 224 to determine if this is step 5 and if it is, the process is repeated using two valves (82 and 84). If it is the last step, the process is terminated.

The calculations occurring in block 222 are shown in detail in FIG. 7 showing that the initial scaling factor is randomly selected to be 0.6 as indicated by block 223′ and the solution to the equation shown adjacent block 224′ is then initially attempted. The data pertaining to the total gas flow represents the parenthetical clause on the left side of this equation where $F_1$ and $K_1$ are constants corresponding to corrections for temperature and pressure conditions and conversion units used to convert the voltage signal from pressure transducer 90 to the dosing gas flow rate respectively.

On the right-hand side of the equation shown in FIG. 7, the sum of IR data for N sample points is taken and where I corresponds to a breakpoint in the concentration curve 12 (FIG. 1) where it is seen as seven such breakpoints are employed to approximate the linear concentration curve for the eight levels of gas dosing employed for linearity correction. The scaling factors are to be determined for each of the levels of concentration to linearize the infrared data corresponding to $S_0$ through $S_7$. For the first segment of the curve, $S_0$ is set to 1 and ratio of flow data to IR data is established. Linearization of IR data is then accomplished by determining the value of $S_1$ at the next seven concentration points by varying $S_I$ from 0.6 to 2 until equation 224′ is satisfied to attain the same ratio as the first segment. This is done at all seven levels to determine eight breakpoints and eight scale factors. This data is determined and stored to be used in the determination of the unknown gas.

As indicated by block 225′, $S_I$ is increased by approximation by, for example, increasing it by a tenth of a point if the equation is relatively close to solution or if the equation of FIG. 7 is not significantly close, $S_I$ can be increased by as much as 0.5. The iterative process through the loop consisting of blocks 224′ and 225′ can be repeated several times in order to ascertain the scaling factor for each gas level of dosing as well as the adjusted breakpoint, which information is then stored into the RAM memory as indicated by block 226.

Next, in the programming sequence, the microprocessor tests (as indicated by block 224 in FIG. 6) whether or not the dosing level is the last step (223) of level 5 in the sequence of eight levels. If it is not the last step or level 5, the pressure-up valve 77 is actuated to increase the flow to the second, third or fourth level of dosing depending upon which level is next in the sequence as indicated by block 225, and the existence of the next level of pressure is tested as indicated by block 232. Valve 77 remains energized until the next pressure level is reached after which it is deenergized as indicated by block 234 and the dosing valve 84 again energized and the sequence consisting of blocks 212 through 222 repeated until the first four levels of dosing have been completed. When level five is reached, the program tests this event as indicated by block 224 and the pressure-down valve 79 is energized as indicated by block 236. Subsequently, after a predetermined time delay as indicated by block 238, valve 72 is again pulsed to purge the system after which the pressure-down valve is deenergized as indicated by block 242 and the pressure-up valve 77 reenergized as indicated by block 225. Once the pressure point for level five is reached as indicated by the test of block 232, the pressure-up valve is deenergized as indicated by block 234 and the program returns to the actuation process indicated by block 212 for the dosing valves 82 and 84. For levels 5 through 8, however, both valves 82 and 84 are actuated to increase the flow rate thereby increasing the dosing levels. The entire process is performed for each of the different specimen gases of interest and in the preferred embodiment eight scaling factors are determined for $CO_2$ and $SO_2$. Once the last scaling factor has been determined and the last breakpoint reached, the program leaves the linearization subroutine as indicated by block 223 and all of the determined contents are transferred into RAM memory as indicated by block 244 and printer 150 (FIG. 8) is actuated to print out the determined linearization constants. The microprocessor then is returned to the main program as indicated by block 248 for utilization of the analyzer.

During use of the analyzer, the stored linearization constants are employed to calculate the actual concentration for displaying concentration levels as they vary according to the level of detected concentration and the scaling factor stored in memory corresponding to the range in which such level falls. Thus, the system of applicant's invention provides a unique method and a valve and manifold structure and system for precisely dosing specimen gas of with known concentration for determining scaling factors for eight different levels of dosing. Such scaling factors are then utilized to correct for linearity in the response curve of the infrared detectors for unknown specimen concentrations incurred during the analysis of unknown specimen materials.

It will become apparent to those skilled in the art that various modifications to the preferred embodiment as described herein can be made by those skilled in the art without departing from the spirit or scope of the invention as defined by the appended claims.

The embodiment of the invention in which an exclusive property or privilege is claimed are defined as follows:

1. For use in an analyzer employed in the analysis of gaseous specimens in which different concentrations of specimen gas are introduced into the flow of gases by dosing to linearize the signals from the detection system of the analyzer, a system for dosing such concentrations of specimen gas comprising:
 a source of specimen gas;
 a manifold having a conduit coupled in the gas flow path of the analyzer;
 means coupled to said manifold for metering specimen gas from said source to said conduit;
 means for detecting the quantity of gas metered into the analyzer; and
 circuit means coupled to said detecting means for determining a scaling factor for a known concentration of specimen gas metered into the analyzer which scaling factor corrects for non-linearities in the detection system of the analyzer.

2. The apparatus as defined in claim 1 wherein said means for metering specimen gas comprises a flow restrictor and means for varying the pressure of specimen gas supplied to said flow restrictor to vary the concentration of gas introduced into the analyzer.

3. The system as defined by claim 2 wherein said means for varying the pressure of specimen gas supplied to said flow restrictor includes a valve and wherein said manifold includes aperture means for mounting said valve and flow restrictor in said manifold adjacent said conduit to provide a minimum volume for rapid control of gas dosed into the analyzer.

4. The apparatus as defined in claim 3 wherein said detecting means comprises a pressure transducer coupled to detect the pressure across said flow restrictor and provide an output signal directly related to the pressure dependent flow through said restrictor.

5. The system as defined in claim 4 wherein said source of specimen gas includes a known mixture of different gases.

6. The system as defined in claim 5 wherein said known mixture of specimen gas comprises a mixture of 95% $CO_2$ and 5% $SO_2$.

7. The system as defined in claim 1 wherein said means for metering specimen gas comprises first and second flow restrictors and means for selectively applying different pressure levels of specimen gas to said first and second flow restrictors to successively provide a plurality of increasing levels of concentration of specimen gas to the analyzer.

8. A method of gas dosing in an analyzer of gaseous specimens for linearizing the analyzer detection system comprising:
 metering a specimen gas having a known purity into the analyzer detection system;
 measuring the flow of specimen gas metered into the analyzer to determine the concentration of specimen gas;
 successively repeating the metering and measuring steps while increasing the metering rate to provide a plurality of known concentration levels of specimen gas to the analyzer; and
 calculating for each level of known concentration of gases, a scaling factor determined by correlating the known concentration with a concentration detected by the analyzer such that the detected concentration at a plurality of levels can be corrected by the scaling factor to provide a linear response for the analyzer detector during use in the analysis of unknown concentrations of gases.

9. The method as defined in claim 8 wherein the metering step comprises supplying specimen gas through a flow restrictor for a predetermined time.

10. The method as defined in claim 9 wherein the step of increasing the metering rate comprises increasing the pressure of gas supplied to the flow restrictor to increase the flow rate of specimen gas.

11. The method as defined in claim 10 wherein the measuring step includes detecting specimen gas pressure across the flow restrictor which pressure is directly related to the flow rate of specimen gas through the restrictor.

12. The method as defined in claim 11 wherein the metering step further comprises the supplying of a known mixture of specimen gases.

13. A system for linearizing the detected concentrations of an analyzer for gaseous specimens employing a detecting system with a nonlinear response comprising:
 means for introducing a plurality of concentration levels of specimen gases into a detecting system;
 means for generating signals representing the amount of gas introduced to determine the concentration of gas introduced;
 means for detecting the introduced levels of known concentrations of specimen gases; and
 computing circuit means coupled to said generating means and to said detecting means for determining a scaling factor for each known concentration level of specimen gas which scaling factor is used to correct for any nonlinear response characteristic of the detecting means.

14. The apparatus as defined in claim 13 wherein said computing circuit means comprises a microprocessor having an algorithm to sum the signals representing the gas introduced and compare such sum with the sum of the detected gas concentrations multiplied by an unknown scaling factor which is approximated and incrementally modified to determine the value of such scaling factor for each level of concentration.

15. The apparatus as defined in claim 14 wherein said microprocessor includes memory circuit means for storing said scaling factors.

16. The system as defined in claim 15 wherein said introducing means comprises:
a source of specimen gas;
a manifold having a conduit coupled in the gas flow path of the analyzer; and
means coupled to said manifold for metering specimen gas from said source to said conduit.

17. The apparatus as defined in claim 16 wherein said means for metering specimen gas comprises a flow restrictor and means for varying the pressure of specimen gas supplied to said flow restrictor to vary the concentration of gas introduced into the analyzer.

18. The apparatus as defined in claim 17 wherein said generating means comprises a pressure transducer coupled to detect the pressure of specimen gas supplied to said flow restrictor and provide said signal representing the amount of gas introduced.

19. A method of linearizing output signals from an infrared detector employed in the analysis of gaseous specimens to provide a predictable linear output signal for different levels of concentrations detected by the infrared detector comprising the steps of:
dosing a known concentration of specimen gas into the infrared detecting system at a plurality of concentration levels;
detecting the concentration levels of gases so dosed and providing output signals representative of the detected concentrations;
generating signals representative of the known quantity of dosing gases introduced into the system; and
calculating for each level of known concentration of gases, a scaling factor determined by correlating the known concentration with the detected concentration such that the detected concentration at a plurality of levels can be corrected by the scaling factor to provide a linear response for the infrared detector during use in the analysis of unknown concentrations of gases.

20. A valve manifold for use in a gas dosing system incorporated in an analyzer for the analysis of gaseous specimens comprising:
a body member having an inlet and an outlet formed therein, said body including a gas flow conduit extending between said inlet and outlet, said body further including a valve seat formed therein and including an aperture communicating with said valve seat and said conduit, said valve seat formed to receive a gas flow restrictor and a valve, said body including second and third apertures, said second aperture communicating with said conduit and said third aperture communicating with said valve seat, and means coupled to said second and third apertures for monitoring the differential pressure between said conduit and gas supplied to said conduit through said valve mounted to said valve seat.

21. The apparatus as defined in claim 20 wherein said body member includes a second valve seat formed therein and including an aperture communicating with said conduit, said second valve seat formed to receive a second valve and a second flow restrictor, means for coupling said valve and said second valve to a source of specimen gas, and means for selectively actuating said valve and said second valve for selectively supplying specimen gas from said source to said conduit.

22. The apparatus as defined in claim 21 wherein said body member includes a third valve seat formed therein and communicating between said conduit and said second aperture, and a third valve mounted to said third valve seat and operable to selectively couple said monitoring means to said conduit to monitor either the pressure across said first and second flow restrictors or to provide a zero pressure reading.

* * * * *

UNITED STATES PATENT AND TRADEMARK OFFICE
CERTIFICATE OF CORRECTION

PATENT NO. : 4,290,296

DATED : September 22, 1981

INVENTOR(S) : Roger L. Bredeweg et al.

It is certified that error appears in the above—identified patent and that said Letters Patent is hereby corrected as shown below:

Column 6, line 36, after "the" insert --valves--.

Signed and Sealed this

Twenty-third Day of March 1982

[SEAL]

Attest:

GERALD J. MOSSINGHOFF

Attesting Officer

Commissioner of Patents and Trademarks